United States Patent [19]

Meyer et al.

[11] 4,368,335

[45] Jan. 11, 1983

[54] N'-(2,6-DICHLORO-4-(SUBSTITUTED-BEN-ZYLAMINO)PHENYL)-N,N-DIMETHYL-FORMAMIDINES

[75] Inventors: Walter E. Meyer, Suffern, N.Y.; Andrew S. Tomcufcik, Old Tappan, N.J.; Joseph W. Marsico, Jr., Pearl River, N.Y.

[73] Assignee: American Cyanamid Company, Stanford, Conn.

[21] Appl. No.: 325,070

[22] Filed: Nov. 25, 1981

[51] Int. Cl.³ .................. C07C 123/00; C07D 317/64
[52] U.S. Cl. .................................. 564/245; 549/437; 549/442
[58] Field of Search ................ 564/245; 549/442, 437

[56] References Cited

U.S. PATENT DOCUMENTS 3,189,648  6/1965  Gerjovich .......................... 564/245

Primary Examiner—Natalie Trousof
Assistant Examiner—L. Hendriksen
Attorney, Agent, or Firm—Edward A. Conroy, Jr.

[57] ABSTRACT

This disclosure describes novel N'-[2,6-dichloro-4-(substituted-benzylamino)phenyl]-N,N-dimethyl-formamidines which possess activity as hypotensive agents and as diuretics.

9 Claims, No Drawings

N'-(2,6-DICHLORO-4-(SUBSTITUTED-BENZYLAMINO)PHENYL)-N,N-DIMETHYL-FORMAMIDINES

BRIEF SUMMARY OF THE INVENTION

This invention relates to new organic compounds and, more particularly, is concerned with novel N'-[2,6-dichloro-4-(substituted-benzylamino)phenyl]-N,N-dimethylformamidines which may be represented by the following structural formula:

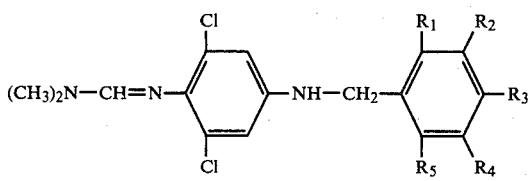

wherein $R_1$ and $R_2$ are each individually selected from the group consisting of hydrogen, fluoro, chloro, bromo, methyl, methoxy and trifluoromethyl; $R_4$ and $R_5$ are each individually selected from the group consisting of hydrogen, chloro and methoxy; $R_3$ is selected from the group consisting of hydrogen, methoxy, phenyl, dimethylamino and diethylamino; and $R_2$ and $R_3$ taken together is methylenedioxy with the proviso that at least two of $R_1$, $R_2$, $R_3$, $R_4$ and $R_5$ are hydrogen. A preferred embodiment of the present invention may be represented by the above structural formula wherein $R_1$, $R_2$, $R_3$ and $R_4$ are as hereinbefore defined and $R_5$ is hydrogen with the proviso that at least one of $R_1$, $R_2$, $R_3$ and $R_4$ is also hydrogen.

The organic bases of this invention form non-toxic acid-addition salts with a variety of pharmacologically acceptable organic and inorganic salt-forming reagents. Thus, acid-addition salts, formed by a mixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel compounds of the present invention may be readily prepared as set forth in the following reaction scheme:

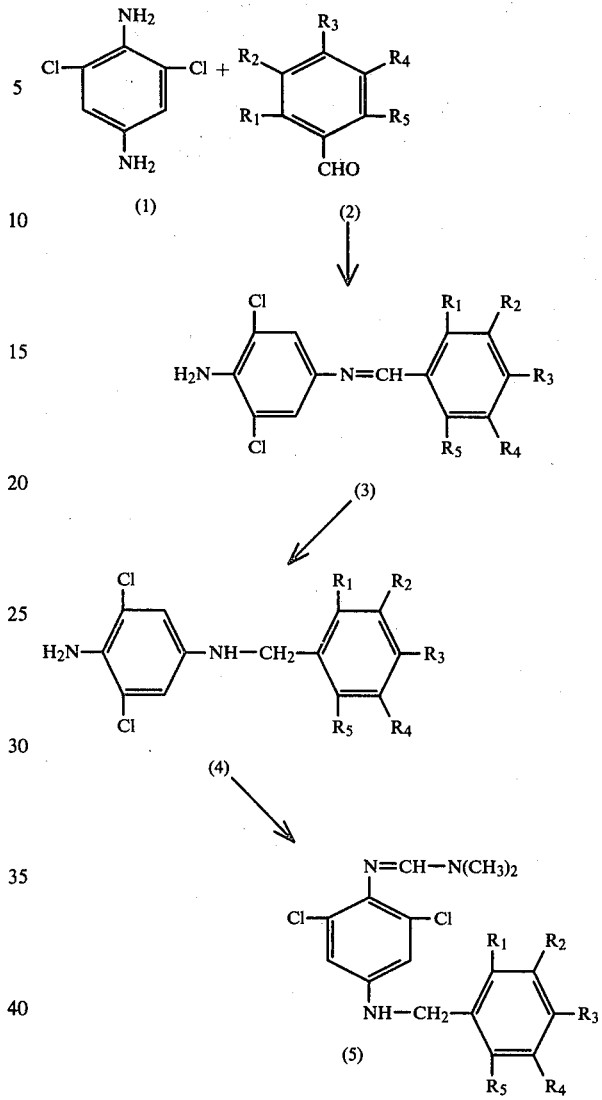

wherein $R_1$, $R_2$, $R_3$, $R_4$ and $R_5$ are as hereinabove defined. In accordance with the above reaction scheme, 2,6-dichloro-p-phenylenediamine (1) is reacted with a benzaldehyde of the general structure (2) to yield the intermediate 2,6-dichloro-$N^4$-benzylidene-p-phenylenediamine compounds (3).

Thus, when 2,6-dichloro-1,4-phenylenediamine and a benzaldehyde of the general structure (2) are dissolved in a solvent such as ethanol or tetrahydrofuran and heated at the reflux temperature for one to 18 hours, with or without the removal of water, compounds of the general structure (3) are obtained. These products may be purified by crystallization from solvents such as ethanol or combinations of solvents such as ethanol and n-hexane.

When the compounds of general structure (3) are dissolved in a solvent such as ethanol or tetrahydrofuran and the solution is hydrogenated in the presence of a noble metal catalyst, preferably finely divided metallic palladium or other metals of the platinum family, the compounds of general structure (4) are obtained. The pure metal may be used or the catalyst may be supported on one of the common carriers such as finely divided alumina, activated charcoal, diatomaceous earth and the like. The hydrogenation may be carried out at temperatures ranging between 0°–50° C. and preferably at room temperature (i.e. 25° C.) and at a hydrogen pressure of about one atmosphere. Or, if compounds of the general structure (3) are dissolved in a solvent such as ethanol or tetrahydrofuran (preferably ethanol) and then treated with a reducing agent such as sodium borohydride, lithium borohydride or, preferably, sodium cyanoborohydride at 0°–50° C. (preferably 25° C.) for 10 minutes to 20 hours (preferably 4 hours) with the pH of the reaction maintained between 4 and 10, compounds of general structure (4) are obtained. When the compounds of general structure (4) are treated with a formamidine forming reagent such as N,N-dimethylformamide dimethylacetal neat, or in an inert solvent, by heating (usually at the reflux temperature) for 4–20 hours, the final products (5) are obtained. After evaporation of the solvents, the products (5) can be purified by crystallization from solvents such as ethanol, or a combination of solvents such as n-hexane and ethanol.

Alternatively, the novel compounds of the present invention may be prepared as set forth in the following reaction scheme:

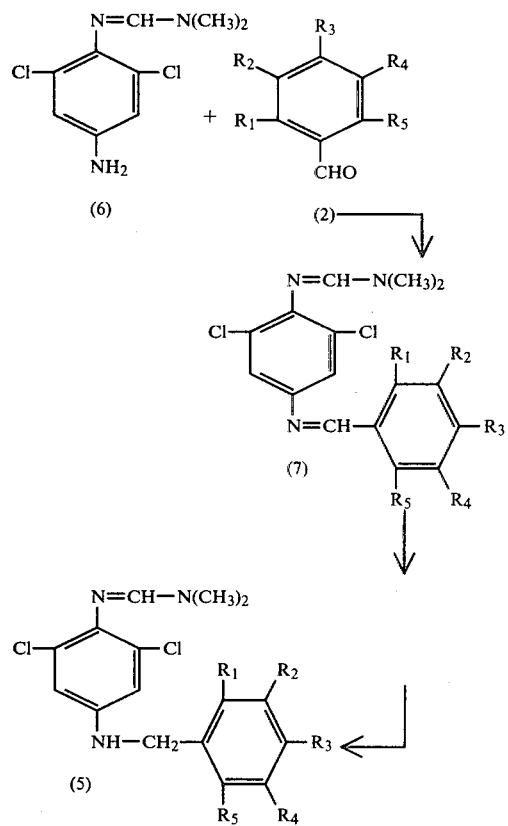

wherein $R_1$, $R_2$, $R_3$, $R_4$ and $R_5$ are as hereinbefore defined. In accordance with the above reaction scheme, N'-(2,6-dichloro-4-aminophenyl)-N,N-dimethylformamidine (6) is dissolved in a solvent such as ethanol and treated at ambient temperature or at the reflux temperature for one to 18 hours, with or without the removal of water, with a benzaldehyde of the general structure (2) to yield the intermediate formamidine compounds (7). These intermediates may be purified by crystallization from common solvents such as ethanol or combinations of solvents such as ethanol and n-hexanes. Alternatively, the compounds (7) may be prepared from compounds of the general structure (3) with formamidine forming reagents such as N,N-dimethylformamide dimethylacetal as previously described.

When the intermediate compounds (7) are dissolved in a solvent such as ethanol or tetrahydrofuran and hydrogenated as previously described the novel compounds of formula (5) are obtained.

The novel compounds of the present invention are physiologically active and, therefore, useful in the pharmaceutical field. In particular, these compounds are useful as either diuretic and/or hypotensive agents.

The novel compounds of the present invention are potent diuretics, producing significant water diuresis and sodium ($Na^+$) loss, but with minimal loss of potassium ($K^+$), as determined in the following procedure.

One to three spontaneously hypertensive rats are dosed by gavage with a test compound at one to 100 mg./kg. of body weight and loaded with 0.9% sodium chloride at 25 ml./kg. of body weight at zero hour. The 0–5 hour urine is collected, its volume measured, and $Na^+$ and $K^+$ concentrations determined. The following compounds have been found to possess significant diuretic activity when tested as described above:

N'-(4-Amino-2,6-dichlorophenyl)-N,N-dimethylformamidine

N'-[2,6-Dichloro-4-(3,4,5-trimethoxybenzylamino)-phenyl]-N,N-dimethylformamidine N'-[2,6-Dichloro-4-(2-chloro-4-dimethylaminobenzylamino)phenyl]-N,N-dimethylformamidine N'-[2,6-Dichloro-4-(m-fluorobenzylamino)phenyl]-N,N-dimethylformamidine hydrochloride N'-[2,6-Dichloro-4-(m-(trifluoromethyl)benzylamino)-phenyl]-N,N-dimethylformamidine hydrochloride N'-[4-(m-Bromobenzylamino)-2,6-dichlorophenyl]-N,N-diylformamidine hydrochloride N'-[2,6-Dichloro-4-(3,5-dichlorobenzylamino)phenyl]-N,N-dimethylformamidine hydrochloride N'-[2,6-Dichloro-4-(4-dimethylamino-2-methoxybenzylamino)phenyl]-N,N-dimethylformamidine N'-[2,6-Dichloro-4-(p-diethylaminobenzylamino)-phenyl]-N,N-dimethylformamidine N'-[2,6-Dichloro-4-(4-dimethylamino-2-methylbenzylamino]phenyl)-N,N-dimethylformamidine N'-[4-(2-Bromo-4-dimethylaminobenzylamino)-2,6-dichlorophenyl]-N,N-dimethylformamidine N'-[4-(3-Bromo-4-dimethylaminobenzylamino)-2,6-dichlorophenyl]-N,N-dimethylformamidine N'-[2,6-Dichloro-4-(4-dimethylamino-2-fluorobenzylamino)phenyl]-N,N-dimethylformamidine The novel compounds of the present invention also possess anti-hypertensive activity at non-toxic doses and as such are useful as hypotensive agents. The hypotensive properties of the compounds of the present invention have been shown when orally administered to mammals, specifically warm-blooded animals as described below.

The novel compounds of the present invention were tested for anti-hypertensive activity in a procedure using spontaneously hypertensive rats (SHR) as follows: One male adult SHR (16–20 weeks old) weighing about 300 grams (Taconic Farms, Germantown, N.Y.) is dosed by gavage with the test compound at one to 100 mg./kg. with 0.9% sodium chloride loading at 25 ml./kg. at zero hour. A second identical dose is given at 24 hours without saline loading and the mean arterial blood pressure (MABP) of the conscious rat is measured directly by femoral artery puncture at 28 hours. A 2nd or 3rd SH rat may be needed depending on the results of the 1st rat [Chan, et al., Pharmacologist, 17, 253 (1975)]. The following representative compounds of the present invention have been shown to possess anti-hypertensive activity when tested as described above.

N'-(4-Amino-2,6-dichlorophenyl)-N,N-dimethylformamidine
N'-[2,6-Dichloro-4-(3,5-dimethoxybenzylamino)-phenyl]-N,N-dimethylformamidine
N'-[2,6-Dichloro-4-(3,4,5-trimethoxybenzylamino)-phenyl]-N,N-dimethylformamidine
N'-[2,6-Dichloro-4-(2-chloro-4-dimethylaminobenzylamino)phenyl]-N,N-dimethylformamidine
N'-[2,6-Dichloro-4-(3-fluoro-4-methoxybenzylamino)-phenyl]-N,N-dimethylformamidine
N'-[2,6-Dichloro-4-(m-fluorobenzylamino)phenyl]-N,N-dimethylformamidine hydrochloride
N'-[2,6-Dichloro-4-(p-phenylbenzylamino)phenyl]-N,N-dimethylformamidine
N'-[4-(m-Bromobenzylamino)-2,6-dichlorophenyl]-N,N-diylformamidine hydrochloride
N'-[2,6-Dichloro-4-(3,5-dichlorobenzylamino)phenyl]-N,N-dimethylformamidine hydrochloride
N'-[2,6-Dichloro-4-(4-dimethylamino-2-methoxybenzylamino)phenyl]-N,N-dimethylformamidine
N'-[2,6-Dichloro-4-(p-diethylaminobenzylamino)-phenyl]-N,N-dimethylformamidine
N'-[2,6-Dichloro-4-(4-dimethylamino-2-methylbenzylamino)phenyl]-N,N-dimethylformamidine
N'-[4-(2-Bromo-4-dimethylaminobenzylamino)-2,6-dichlorophenyl]-N,N-dimethylformamidine The novel compounds of the present invention have thus been shown to be valuable diuretic agents of low toxicity when administered orally. The amount of a single dose or of a daily dose will vary but should be such as to give a proportionate dosage of from about one mg. to about 1000 mg. per day for a subject of about 70 kg. body weight. The dosage regimen may be adjusted to provide the optimum therapeutic response, for example, doses of 25–250 mg. may be administered on a four times per day regimen, or the dose may be proportionately increased as indicated by the exigencies of the therapeutic situation.

The novel compounds of the present invention have also been found to be highly useful for lowering elevated blood pressure in mammals when administered in amounts ranging from about 0.4 mg. to about 10.0 mg. per kg. of body weight per day. A preferred dosage regimen for optimum results would be from about 7.0 mg. to about 175 mg. per dose. Such dosage units are employed that a total of from about 28 mg. to about 700 mg. of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as the intravenous route.

The compounds of the present invention may be administered as active components of compositions in unit dosage form such as tablets, pills, capsules, powders, granules, oral or parenteral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolyment together with known materials contributing to the enteric properties of the coating.

Compositions according to the present invention having the desired clarity, stability and adaptability for parenteral use are obtained by dissolving from 0.01% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes, are for example, myristyl-gamma-picolinium chloride, benzalkonium chloride, phenethyl alcohol, p-chlorphenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

The novel compounds of the present invention are adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention.

The invention will be described in greater detail in conjunction with the following specific examples.

EXAMPLE 1

N'-(4-Amino-2,6-dichlorophenyl)-N,N-dimethylformamidine

A mixture of 20.7 g. of 2,6-dichloro-p-nitroaniline and 15 ml. of N,N-dimethylformamide dimethylacetal in 125 ml. of dimethylformamide is heated on a steam bath for 4 hours. The reaction mixture is cooled at $-10°$ C. and the precipitate is collected by filtration. The product is washed with isopropyl alcohol and dried to give 21.5 g. of N'-(2,6-dichloro-4-nitrophenyl)-N,N-dimethylformamidine, m.p. 164°–166° C.

A 540 g. amount of stannous chloride is dissolved in 450 ml. of concentrated hydrochloric acid with stirring. The solution is cooled to 10° C. in an ice bath and 155 g. of N'-(2,6-dichloro-4-nitrophenyl)-N,N-dimethylformamidine (prepared as described above) is added portionwise, with stirring, at a rate to maintain the reaction temperature at 75° C. The reaction mixture is allowed to stand at room temperature for 18 hours, then is filtered. The filter cake is suspended in 200 ml. of ice water and concentrated sodium hydroxide is added until the reaction mixture is alkaline. The reaction mixture is filtered and the insolubles are collected and extracted with chloroform. The chloroform extracts are evaporated in vacuo to yield 102 g. of the product of the Example as pale yellow crystals, m.p. 121°–126° C.

EXAMPLE 2

N'-[2,6-Dichloro-4-(3,5-dimethoxybenzylamino)-phenyl]-N,N-dimethylformamidine

A mixture of 5.3 g. of 2,6-dichloro-p-phenylenediamine and 4.98 g. of 3,5-dimethoxybenzaldehyde in 100 ml. of ethanol is heated on a steam bath, solution occurs, followed by crystallization. Warming is continued on the steam bath for 16 hours. The reaction mixture is cooled, 50 ml. of glacial acetic acid and 500 mg. of platinum oxide are added and the mixture is hydrogenated in a Parr apparatus at 40 p.s.i. for 15 minutes. The mixture is filtered and washed with ethanol, then the combined filtrate and washings are evaporated to dryness. The residue is treated with 200 ml. of saturated sodium carbonate then is extracted twice with 200 ml. of ethyl acetate. The combined extract is evaporated to dryness. The residue is dissolved in methanol and the solution is cooled at 5° C. to provide crystals. The crystals are collected by filtration and washed with methanol to give 7.8 g. of product. This product is heated at reflux with 20 ml. of N,N-dimethylformamide dimethylacetal for 18 hours. The resulting solution is evaporated to an amber syrup. The syrup is treated with ether/hexane to crystallize 7.1 g. of the product of the Example as colorless needles, m.p. 124°–125° C.

EXAMPLE 3

N'-[2,6-Dichloro-4-(3,4,5-trimethoxybenzylamino)-phenyl]-N,N-dimethylformamidine A mixture of 5.3 g. of 2,6-dichloro-p-phenylenediamine in 50 ml. of warm ethanol and 5.9 g. of 3,4,5-trimethoxybenzaldehyde in 50 ml. of warm ethanol is stirred for 2 hours, then filtered. The filter cake, dissolved in 50 ml. of tetrahydrofuran containing 500 mg. of platinum oxide, is hydrogenated in a Parr apparatus at 47 p.s.i. until no more hydrogen is absorbed. The reaction mixture is filtered and washed with ethanol. The filtrate is evaporated to a syrup which is dissolved in 25 ml. of methanol. The product is crystallized, collected by filtration and washed with cold methanol to give 7.0 g. of 2,6-dichloro-$N^4$-(3,4,5-trimethoxybenzyl)-p-phenylenediamine as yellow crystals, m.p. 96°–97° C.

A 5.0 g. amount of the preceding compound and 20 ml. of N,N-dimethylformamide dimethylacetal is refluxed for 18 hours. The reaction mixture is evaporated to give an amber syrup. The syrup is dissolved in 50 ml. of methanol and water is added until turbid. The mixture is chilled at 5° C. to provide crystals. The crystals are collected and washed with chilled 50% methanol/water to yield 5.84 g. of the product of the Example, m.p. 137°–138.5° C.

EXAMPLE 4

N'-[2,6-Dichloro-4-(2-chloro-4-dimethylaminobenzylamino)phenyl]-N,N-dimethylformamidine A mixture of 18.3 g. of 2-chloro-4-dimethylaminobenzaldehyde and 17.7 g. of 2,6-dichlorophenylenediamine in 200 ml. of ethanol is refluxed for 18 hours. The reaction mixture is evaporated to dryness. The residue is crystallized from a mixture of ethanol and water. The product is collected by filtration and washed with ethanol/water, then dried to give 3.7 g. of 2,6-dichloro-$N^4$-(2-chloro-4-dimethylaminobenzylidene)-p-phenylenediamine as mustard colored crystals, m.p. 139°–140° C.

An 8.0 g. amount of the preceding compound (prepared as described above) is dissolved in 200 ml. of tetrahydrofuran with stirring, then several grams of lithium borohydride are added over a one hour period and the mixture is allowed to stand at room temperature for 16 hours. The mixture is evaporated to an oil, water and chloroform are added and the layers are separated after decomposition of the excess hydride is complete. The chloroform layer is dried over magnesium sulfate, filtered and evaporated in vacuo to give a syrup which is crystallized from a mixture of ethyl ether and n-hexane. The crystals are collected by filtration and washed with n-hexane to give 6.5 g. of 2,6-dichloro-$N^4$-(2-chloro-4-dimethylaminobenzyl)-p-phenylenediamine as yellow crystals, m.p. 91°–94° C.

A 4.0 g. amount of the above compound in 25 ml. of N,N-dimethylformamide dimethylacetal is refluxed for 18 hours. The reaction mixture solvent is evaporated to give a crystalline residue. The residue is dissolved in 125 ml. of boiling ethanol then is allowed to stand at 5° C. The crystallized material is collected by filtration and washed with ethanol to yield 2.5 g. of the product of the Example as yellow crystals, m.p. 177°–178° C.

EXAMPLE 5

N'-[2,6-Dichloro-4-(3-fluoro-4-methoxybenzylamino)-phenyl]-N,N-dimethylformamidine A 7.0 g. amount of N'-(4-amino-2,6-dichlorophenyl)-N,N-dimethylformamidine (Example 1) and 4.6 g. of 3-fluoro-p-anisaldehyde are each dissolved separately in 25 ml. of warm methanol and then combined. The mixture is cooled at 5° C. The crystallized product is collected and washed with ether to provide 8.2 g. of N'-[2,6-dichloro-4-[(3-fluoro-4-methoxybenzylidene)amino]phenyl]-N,N-dimethylformamidine as yellow crystals, m.p. 139°–141° C.

A 4.0 g. amount of N'-[2,6-dichloro-4-[(3-fluoro-4-methoxybenzylidene)amino]phenyl]-N,N-dimethylformamidine is dissolved in 100 ml. of warm tetrahydrofuran, then 500 mg. of platinum oxide that has been wetted with water is added and the mixture is hydrogenated in a Parr apparatus for 15 minutes. The reaction mixture is filtered and washed with tetrahydrofuran. The clear yellow solution is evaporated in vacuo to crystallize a solid. The solid is recrystallized from ethanol, filtered and washed with a small amount of ether to provide 2.0 g. of the desired product as granular yellow crystals, m.p. 138°–140° C.

EXAMPLE 6

N'-[2,6-Dichloro-4-(m-fluorobenzylamino)phenyl]-N,N-dimethylformamidine hydrochloride A 10.6 g. amount of 2,6-dichloro-p-phenylenediamine and 7.4 g. of m-fluorobenzaldehyde are dissolved in 100 ml. of absolute ethanol. The solution is refluxed for 5 hours then cooled in an ice bath at 5° C. for 18 hours. The mixture is filtered and the precipitate is washed with ether to give 11.8 g. of 2,6-dichloro-$N^4$-m-fluorobenzylidene-p-phenylenediamine as grey crystals, m.p. 102°–103° C.

The above filtrate and washings are combined and evaporated to provide additional crystalline product. This material is dissolved in 100 ml. of anhydrous tetrahydrofuran, then over a one hour period there is added 1–2 g. of lithium borohydride with stirring. Stirring is continued for 18 hours then the solution is evaporated to dryness and 100 ml. of chloroform and 50 ml. of water is added to the residue. The mixture is stirred for one hour and the layers are separated. The chloroform layer is dried over magnesium sulfate and the solvent is evaporated to yield 1.0 g. of 2,6-dichloro-$N^4$-m-fluorobenzyl-p-phenylenediamine as bright yellow crystals, m.p. 60°–61° C.

The entire 1.0 g. amount of the preceding product and 15 ml. of N,N-dimethylformamide dimethylacetal is refluxed for 18 hours. The reaction mixture is evaporated to a pale yellow syrup, the syrup is redissolved in 3 ml. of ethanol, then ether is added followed by 3 ml. of 3.6 N ethanolic hydrochloric acid. The solvents are evaporated and the residue is recrystallized from ethanol to give 1.0 g. of the product of the Example as colorless granular crystals, m.p. 239°–241° C. (dec.).

Alternatively, the preparation of the title compound can be achieved by the reaction of the above 2,6-dichloro-$N^4$-m-fluorobenzylidene-p-phenylenediamine with excess dimethylformamide dimethylacetal at the reflux point for 18 hours, removal of excess reagent to yield the crude N'-[2,6-dichloro-4-(m-fluorobenzylideneamino)phenyl]-N,N-dimethylformamidine as a yellow solid, and reduction with lithium borohydride in tetrahydrofuran solution.

EXAMPLE 7

N'-[2,6-Dichloro-4-[m-(trifluoromethyl)benzylamino]-phenyl]-N,N-dimethylformamidine hydrochloride A mixture of 8.9 g. of 2,6-dichloro-p-phenylenediamine and 8.7 g. of m-trifluoromethylbenzaldehyde in 50 ml. of absolute ethanol is refluxed for 5 hours. The solvent is evaporated, then ethanol is added to the solid cake followed by n-hexane. The mixture is filtered and the precipitate is washed with n-hexane until the wash is clear to give 11.5 g. of 2,6-dichloro-$N^4$-$\alpha,\alpha,\alpha$-trifluoro-m-benzylidene-p-phenylenediamine as tan needles, m.p. 124°–125° C.

A mixture of 10.0 g. of the preceding compound and 500 mg. of 10% palladium-on-carbon catalyst in 100 ml. of tetrahydrofuran is hydrogenated in a Parr shaker at room temperature for 3 hours with a pressure drop from 48 p.s.i. to 22 p.s.i. The mixture is filtered and washed with tetrahydrofuran. The dark filtrate is evaporated to a syrup. The syrup is dissolved in ethanol then n-hexane is added until turbid. The mixture is cooled and 20 ml. of 4.1 N ethanolic hydrochloric acid is added. The crude product is recrystallized from ethanol to give 5.3 g. of 2,6-dichloro-$N^4$-[m-(trifluoromethyl)benzyl]-p-phenylenediamine hydrochloride as colorless crystals, m.p. >210° C. (dec.).

A mixture of 5.0 g. of the above product and 25 ml. of N sodium hydroxide is extracted with 100 ml. of chloroform and 50 ml. of methylene chloride. The extracts are dried over magnesium sulfate and evaporated in vacuo to give a syrup, then 25 ml. of N,N-dimethylformamide dimethylacetal is added and the mixture is refluxed for 18 hours. The reaction solution is evaporated to a clear yellow syrup. The syrup is dissolved in 10 ml. of ethanol and n-hexane is added until turbid, then 15 ml. of 4.1 N ethanolic hydrochloric acid is added, the product collected, to provide 5.6 g. of the product of the Example as pink crystals, m.p. 214°–217° C. (dec.).

EXAMPLE 8

N'-[2,6-Dichloro-4-(p-phenylbenzylamino)phenyl]-N,N-dimethylformamidine

A 17.7 g. amount of 2,6-dichloro-1,4-phenylenediamine is dissolved in 50 ml. of refluxing ethanol and 18.2 g. of 4-biphenylcarboxaldehyde is dissolved in 15 ml. of hot ethanol and added to the above solution. The orange-yellow solution is refluxed for 18 hours, then is cooled and filtered. The product is washed with n-hexane to provide 35.0 g. of 2,6-dichloro-$N^4$-p-phenylbenzylidene-p-phenylenediamine as bright yellow needles, m.p. 108°–110° C.

A mixture of 13.6 g. of 2,6-dichloro-$N^4$-p-phenylbenzylidene-p-phenylenediamine and 1.0 g. of 10% palladium-on-carbon catalyst in 100 ml. of tetrahydrofuran is hydrogenated in a Parr shaker at room temperature with a pressure drop from 44 p.s.i. to 15 p.s.i. The mixture is filtered and washed with tetrahydrofuran. The filtrate is evaporated to a syrup which is treated with ethanol/hexane to crystallize the product. The product is collected and washed with n-hexane to give 9.4 g. of 2,6-dichloro-$N^4$-p-phenylbenzyl-p-phenylenediamine as pale yellow crystals, m.p. 110°–111° C.

A 6.9 g. amount of the above product in 21 ml. of N,N-dimethylformamide dimethylacetal is refluxed for 5 hours then is allowed to stand at room temperature. The solvent is evaporated in vacuo and the solid is dissolved in 300 ml. of refluxing ethanol. The ethanol solution is evaporated to 100 ml. and cooled at 5° C. The crystallized product is collected by filtration and washed with ethanol/n-hexane to yield 4.4 g. of the product of the Example as pale yellow crystals, m.p. 165°–168° C.

EXAMPLE 9

N'-[4-(m-Bromobenzylamino)-2,6-dichlorophenyl]-N,N-dimethylformamidine hydrochloride A 17.7 g. amount of 2,6-dichloro-1,4-phenylenediamine is dissolved in 50 ml. of absolute ethanol, then 18.5 g. of m-bromobenzaldehyde is added. Crystallization of a product takes place within one minute, then n-hexane is added. The product is collected by filtration to give 31.0 g. of $N^4$-m-bromobenzylidene-2,6-dichloro-p-phenylenediamine as pale yellow crystals, m.p. 136°–138° C.

A 17.3 g. amount of $N^4$-m-bromobenzylidene-2,6-dichloro-p-phenylenediamine is dissolved in 100 ml. of warm tetrahydrofuran, then 1.0 g. of platinum oxide is added and the mixture is hydrogenated in a Parr apparatus. Reduction is complete after 5 minutes with 4.5 p.s.i. consumed. The reaction mixture is filtered and washed with tetrahydrofuran. The pale yellow filtrate is evaporated to a syrup. The syrup is dissolved in ethanol, then hexane is added and the solution is treated with 25 ml. of 4.1 N ethanolic hydrochloric acid. The product is collected by filtration and washed with n-hexane to give 21.8 g. of $N^4$-m-bromobenzyl-2,6-dichloro-p-phenylenediamine hydrochloride as orange crystals, m.p. 192°–195° C. (dec.).

A mixture of 10.0 g. of the preceding compound, 20 ml. of water, and 10 ml. of 10 N sodium hydroxide is extracted with two 50 ml. portions of chloroform. The combined extract is dried over magnesium sulfate and evaporated to a syrup. The syrup is refluxed with 25 ml. of N,N-dimethylformamide dimethylacetal for 18 hours. The reaction mixture solvent is removed in vacuo to give an amber syrup which is dissolved in 20 ml. of warm ethanol. The addition of 20 ml. of 4.1 N ethanolic hydrochloric acid gives 10.0 g. of the product of the Example as colorless crystals, m.p. 217°–219° C.

EXAMPLE 10

N'-[2,6-Dichloro-4-(3,5-dichlorobenzylamino)phenyl]-N,N-dimethylformamidine hydrochloride A mixture of 13.3 g. of 2,6-dichloro-p-phenylenediamine and 13.1 g. of 3,5-dichlorobenzaldehyde in 100 ml. of absolute ethanol is refluxed for 18 hours. The mixture is cooled and hexane is added. The product is collected by filtration and is washed with hexane until the wash is clear to give 24.3 g. of 2,6-dichloro-$N^4$-3,5-dichlorobenzylidene-p-phenylenediamine as mustard colored crystals, m.p. 194°–195° C.

A mixture of 13.8 g. of 2,6-dichloro-$N^4$-3,5-dichlorobenzylidene-p-phenylenediamine, 150 ml. of warm tetrahydrofuran and 1.0 g. of 10% palladium-on-carbon catalyst is hydrogenated in a Parr shaker at room temperature for 3 hours. The reaction mixture is cooled, filtered, and evaporated in vacuo to give a dark syrup. The addition of ethanol and n-hexane gives 8.3 g. of crude product. Recrystallization from heptane gives 4.7 g. of 2,6-dichloro-$N^4$-3,5-dichlorobenzyl-p-phenylenediamine as crystals, m.p. 133°–135° C.

A 3.0 g. amount of the preceding product in 20 ml. of N,N-dimethylformamide dimethylacetal is refluxed for 5 hours. The mixture is evaporated in vacuo to give a syrup. The syrup is dissolved in 10 ml. of ethanol and 30 ml. of 4.1 N ethanolic hydrochloric acid is added. After the addition of ether the crystals are collected by filtration and washed with ethanol/ether then ether to give 1.6 g. of the desired product as off-white crystals, m.p. 240°–242° C. (dec.).

EXAMPLE 11

N'-[2,6-Dichloro-4-[(4-dimethylamino-2-methoxybenzyl)-amino]phenyl]-N,N-dimethylformamidine An 8.0 g. amount of 2,6-dichloro-p-phenylenediamine is dissolved in 50 ml. of warm ethanol then 8.1 g. of 4-dimethylamino-2-methoxybenzaldehyde is added and the mixture is heated at reflux for 5 hours. The solution is cooled to room temperature and crystallization is induced by the addition of several drops of n-hexane. Filtration gives 9.2 g. of 2,6-dichloro-$N^4$-(4-dimethylamino-2-methoxybenzylidene)-p-phenylenediamine as bright yellow crystals, m.p. 137°–139° C.

A 5.0 g. amount of 2,6-dichloro-$N^4$-(4-dimethylamino-2-methoxybenzylidene)-p-phenylenediamine is slurried in 100 ml. of methanol. To this mixture is added, with stirring, over a 30 minute period, 1.2 g. of sodium borohydride. After an additional 30 minutes of stirring, 3.6 g. of 2,6-dichloro-N'-(4-dimethylamino-2-methoxybenzyl)-p-phenylenediamine is collected by filtration as yellow crystals, m.p. 111°–113° C.

A 3.0 g. amount of the above material in 15 ml. of N,N-dimethylformamide dimethylacetal is heated at the reflux temperature for 6 hours. The mixture is evaporated in vacuo to a crystalline residue. Recrystallization from 15 ml. of ethanol gives 1.7 g. of N'-[2,6-dichloro-4-[(4-dimethylamino-2-methoxybenzyl)amino]phenyl]-N,N-dimethylformamidine as granular, yellow crystals, m.p. 160°–162° C.

EXAMPLE 12

N'-[2,6-Dichloro-4-(p-diethylaminobenzylamino)-phenyl]-N,N-dimethylformamidine

A 10.8 g. amount of 2,6-dichloro-p-phenylenediamine is dissolved in 75 ml. of warm ethanol, then 10.8 g. of p-diethylaminobenzaldehyde is added and the mixture is refluxed for 18 hours. The reaction mixture is diluted to one liter with n-hexane. The solution is evaporated to a dark amber syrup and crystallized from a mixture of toluene and hexane, to give 3.7 g. of 2,6-dichloro-$N^4$-(p-diethylaminobenzylidene)-p-phenylenediamine as light yellow crystals, m.p. 56°–57° C.

A 6.7 g. amount of 2,6-dichloro-$N^4$-(p-diethylaminobenzylidene)-p-phenylenediamine (prepared as described above) is dissolved in 50 ml. of dry tetrahydrofuran (dried over 3 A molecular sieves). Then over a 5 minute period with stirring is added 1.0 g. of lithium borohydride. The mixture is covered and stirred for 18 hours.

The reaction mixture is filtered through diatomaceous earth and evaporated to a syrup. Water and chloroform are added to the syrup and the mixture is stirred for 2 hours. The chloroform layer is evaporated in vacuo to give a syrup which is crystallized from ethanol to give 1.2 g. of 2,6-dichloro-$N^4$-(p-diethylaminobenzyl)-p-phenylenediamine as colorless crystals, m.p. 120° C. (dec.).

A 5.6 g. amount of 2,6-dichloro-$N^4$-(p-diethylaminobenzyl)-p-phenylenediamine (prepared as described above) and 15 ml. of N,N-dimethylformamide dimethylacetal are refluxed for 18 hours. The reaction mixture is evaporated to a pale yellow syrup. The syrup is dissolved in 20 ml. of ethanol, treated with activated carbon and filtered. The filtrate is diluted to 250 ml. with n-hexane to provide 4.1 g. of the product of the Example as colorless needles, m.p. 98°–99° C.

EXAMPLE 13

N'-[2,6-Dichloro-4-(4-dimethylamino-2-methylbenzylamino)phenyl]-N,N-dimethylformamidine A 25.0 g. amount of N,N-dimethyl-m-toluidine is formulated with Vilsmeier reagent (N,N-dimethylformamide-phosphorus oxychloride) to give 19.0 of 4-dimethylamino-o-tolualdehyde as pale yellow crystals, m.p. 64°–65° C. A 10.6 g. amount of recrystallized 2,6-dichloro-p-phenylenediamine is dissolved in 50 ml. of warm ethanol, then 9.8 g. of 4-dimethylamino-o-tolualdehyde is added and the mixture is heated at a simmer for 3 hours. The mixture is allowed to stand at room temperature for 16 hours, then is evaporated to dryness. The residue is recrystallized from ethanol/n-hexane, filtered and washed with ethanol/hexane to yield 12.0 g. of 2,6-dichloro-$N^4$-(4-dimethylamino-2-methylbenzylidene)-p-phenylenediamine as mustard colored needles, m.p. 92°–93° C.

A 6.4 g. amount of 2,6-dichloro-$N^4$-(4-dimethylamino-2-methylbenzylidene)-p-phenylenediamine is slurried in 100 ml. of methanol. To this mixture is added, with stirring, over a 2 hour period 2.0 g. of sodium borohydride. Solution occurs and the mixture is stirred at room temperature for 18 hours. The solution is evaporated to dryness. The residue is extracted from water with two 100 ml. portions of chloroform. The combined extracts are dried over magnesium sulfate and evaporated to a syrup which is crystallized in the presence of ethanol to give 5.3 g. of 2,6-dichloro-$N^4$-(4-dimethylamino-2-methylbenzyl)-p-phenylenediamine as tan plates, m.p. 108°–109° C.

A 3.0 g. amount of the preceding compound in 15 ml. of N,N-dimethylformamide dimethylacetal is refluxed for 6 hours. The mixture is cooled and evaporated in vacuo to a dark amber syrup. Crystallization from ethanol and n-hexane gives 2.4 g. of the product of the Example as golden plates, m.p. 166°–168° C.

EXAMPLE 14

N'-[4-(2-Bromo-4-dimethylaminobenzylamino)-2,6-dichlorophenyl]-N,N-dimethylformamidine A 31.0 g. amount of 3-bromo-dimethylaniline and 20 ml. of dry N,N-dimethylformamide is added over a 20 minute period to a cold stirred solution of Vilsmeier reagent (N,N-dimethylformamide-phosphorus oxychloride) to give 28.5 g. of pale yellow crystals. The product is recrystallized from hexane, filtered and washed with hexane to give 20.3 g. of 2-bromo-4-dimethylaminobenzaldehyde as colorless needles, m.p. 86°–88° C.

A 10.6 g. amount of 2,6-dichloro-p-phenylenediamine is dissolved in 50 ml. of warm ethanol and 13.7 g. of the preceding aldehyde is added. The reaction mixture is refluxed for one hour then is allowed to stand at room temperature. The solid is collected by filtration to yield 21 g. of $N^4$-(2-bromo-4-dimethylaminobenzylidene)-2,6-dichloro-p-phenylenediamine as mustard colored crystals, m.p. 152°–153° C.

An 8.1 g. amount of $N^4$-(2-bromo-4-dimethylaminobenzylidene)-2,6-dichloro-p-phenylenediamine is stirred in 125 ml. of methanol. To this suspension is added with stirring, portionwise, over a one hour period 1.3 g. of sodium borohydride. The reaction mixture sets to a solid and is filtered and washed with water. The aqueous phase is extracted with 200 ml. of chloroform which is dried over magnesium sulfate and evaporated to give an oil. Crystallization from ethanol gives 2.7 g. of $N^4$-(2-bromo-4-dimethylaminobenzyl)-2,6-dichloro-p-phenylenediamine as bright yellow crystals, m.p. 133°–135° C.

The preceding product (2.7 g.) is refluxed for 5 hours in 25 ml. of N,N-dimethylformamide dimethylacetal. The reaction solution is evaporated in vacuo to yield yellow crystals. The material is recrystallized from ethanol/n-hexane to give 2.5 g. of the desired product as yellow crystals, m.p. 135°–137° C.

EXAMPLE 15

N'-[4-(3-Bromo-4-dimethylaminobenzylamino)-2,6-dichlorophenyl]-N,N-dimethylformamidine An 8.8 g. amount of 2,6-dichloro-p-phenylenediamine is dissolved in 40 ml. of ethanol by refluxing, then 11.4 g. of 3-bromo-4-dimethylaminobenzaldehyde [prepared by the method of Brady and Truszkowske, J. Chem. Soc., 123, 2438 (1923)] in 10 ml. of ethanol is added. The mixture is refluxed for 6 hours, then cooled to give crystals. Washing with n-hexane gives 17.3 g. of $N^4$-(3-bromo-4-dimethylaminobenzylidene)-2,6-dichloro-p-phenylenediamine as pale yellow crystals, m.p. 138°–140° C.

A 3.9 g. amount of $N^4$-(3-bromo-4-dimethylaminobenzylidene)-2,6-dichloro-p-phenylenediamine is stirred as a slurry in 100 ml. of methanol. To the slurry is added with stirring, portionwise over a one hour period, 1.0 g. of sodium borohydride. The resulting solution is covered and stirred at room temperature for 18 hours. The reaction mixture is evaporated to dryness, water is added and the mixture extracted twice with 75 ml. of chloroform. Evaporation of the chloroform yields an amber syrup which crystallizes from ethanol to give 3.0 g. of $N^4$-(3-bromo-4-dimethylaminobenzyl)-2,6-dichloro-p-phenylenediamine as pale yellow needles, m.p. 98°–99° C.

A 2.5 g. amount of the preceding product in 15 ml. of N,N-dimethylformamide dimethylacetal is refluxed for 18 hours. The solution is evaporated to an amber syrup. The syrup is treated with hexane and ether to give 1.4 g. of the product of the Example as pale yellow rosettes, m.p. 109°–110° C.

EXAMPLE 16

N'-[2,6-Dichloro-4-[(4-dimethylamino-2-fluorobenzyl)-amino]phenyl]-N,N-dimethylformamidine An 8.8 g. amount of 2,6-dichloro-p-phenylenediamine is dissolved in 100 ml. of refluxing ethanol. Then 8.4 g. of 4-dimethylamino-2-fluorobenzaldehyde [prepared by the method of J. Org. Chem., 25, 2053 (1960)] is added, the mixture is refluxed for 4 hours, cooled, filtered and washed with cold ethanol, ethanol-hexane then hexane to give 12.0 g. of 2,6-dichloro-$N^4$-(4-dimethylamino-2-fluorobenzylidene)-p-phenylenediamine as crystals, m.p. 127°–128° C.

To a stirred slurry of 5.0 g. of 2,6-dichloro-$N^4$-(4-dimethylamino-2-fluorobenzylidene-p-phenylenediamine is added one g. of sodium borohydride, portionwise, over a 30 minute period. The reaction mixture is evaporated to a dryness after stirring at room temperature for 18 hours. Water is added and the mixture is extracted with chloroform. The chloroform extract is evaporated to give a tan solid which is crystallized from a mixture of ether and n-hexane to give 3.9 g. of 2,6-dichloro-$N^4$-(4-dimethylamino-2-fluorobenzyl)-p-phenylenediamine as pale yellow crystals, m.p. 114°–115° C.

A 3.5 g. amount of the preceding product in 15 ml. of N,N-dimethylformamide dimethylacetal is refluxed for 6 hours. The mixture is evaporated to a syrup. The syrup is crystallized from ethanol/n-hexane/ether to give 2.2 g. of the desired product, m.p. 118°–120° C.

We claim:

1. A compound selected from the group consisting of those of the formula:

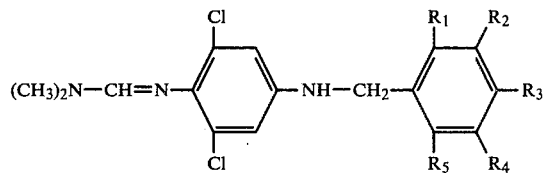

wherein $R_1$ and $R_2$ are the same or different and are hydrogen, fluoro, chloro, bromo, methyl, methoxy or trifluoromethyl; $R_4$ and $R_5$ are the same or different and are hydrogen, chloro or methoxy; $R_3$ is hydrogen, methoxy, phenyl, dimethylamino or diethylamino; and $R_2$ and $R_3$ taken together is methylenedioxy with the proviso that at least two of $R_1$, $R_2$, $R_3$, $R_4$ and $R_5$ are hydrogen; and the pharmacologically acceptable acid-addition salts thereof.

2. The compound according to claim 1 wherein $R_1$ and $R_5$ are both hydrogen and $R_2$, $R_3$ and $R_4$ are all methoxy; N′-[2,6-dichloro-4-(3,4,5-trimethoxybenzylamino)phenyl]-N,N-dimethylformamidine.

3. The compound according to claim 1 wherein $R_1$ is chloro, $R_3$ is dimethylamino and $R_2$, $R_4$ and $R_5$ are all hydrogen; N′-[2,6-dichloro-4-(2-chloro-4-dimethylaminobenzylamino)phenyl]-N,N-dimethylformamidine.

4. The compound according to claim 1 wherein $R_2$ is fluoro, $R_3$ is methoxy and $R_1$, $R_4$ and $R_5$ are all hydrogen; N′-[2,6-dichloro-4-(3-fluoro-4-methoxybenzylamino)phenyl]-N,N-dimethylformamidine.

5. The compound according to claim 1 wherein $R_2$ is fluoro and $R_1$, $R_3$, $R_4$ and $R_5$ are all hydrogen; N′-[2,6-dichloro-4-(m-fluorobenzylamino)phenyl]-N,N-dimethylformamidine hydrochloride.

6. The compound according to claim 1 wherein $R_1$ is bromo and $R_2$, $R_3$, $R_4$ and $R_5$ are all hydrogen; N′-[4-(o-bromobenzylamino)-2,6-dichlorophenyl]-N,N-dimethylformamidine hydrochloride.

7. The compound according to claim 1 wherein $R_1$ is bromo, $R_3$ is dimethylamino and $R_2$, $R_4$ and $R_5$ are all hydrogen; N′-[4-(2-bromo-4-dimethylaminobenzylamino)-2,6-dichlorophenyl]-N,N-dimethylformamidine.

8. The compound according to claim 1 wherein $R_1$ is methoxy, $R_3$ is dimethylamino and $R_2$, $R_4$ and $R_5$ are all hydrogen; N′-[2,6-dichloro-4-(4-dimethylamino-2-methoxybenzylamino)phenyl]-N,N-dimethylformamidine.

9. A compound selected from the group consisting of N′-(4-amino-2,6-dichlorophenyl)-N,N-dimethylformamidine and the pharmacologically acceptable acid-addition salts thereof.

* * * * *